United States Patent [19]

John

[11] 4,171,696
[45] Oct. 23, 1979

[54] PREVENTION OF DISTORTION OF BRAINWAVE DATA DUE TO EYE MOVEMENT OR OTHER ARTIFACTS

[76] Inventor: E. Roy John, 930 Greacen La., Mamaroneck, N.Y. 10546

[21] Appl. No.: 873,119

[22] Filed: Jan. 30, 1978

[51] Int. Cl.² ............................................... A61B 5/04
[52] U.S. Cl. .................................................. 128/731
[58] Field of Search ............ 128/2.1 B, 2.1 M, 2.1 R, 128/2.06 B

[56] References Cited

U.S. PATENT DOCUMENTS

| | | | |
|---|---|---|---|
| 2,902,030 | 9/1959 | Kennedy et al. | 128/2.1 M |
| 3,621,836 | 11/1971 | Nagatomi | 128/2.1 B |
| 3,656,474 | 4/1972 | Gentry et al. | 128/2.1 M |
| 3,774,593 | 11/1973 | Hakata et al. | 128/2.1 B |
| 3,837,331 | 9/1974 | Ross | 128/2.1 B |
| 3,880,144 | 4/1975 | Coursin et al. | 128/2.1 B |

Primary Examiner—W. E. Kamm
Attorney, Agent, or Firm—Eliot S. Gerber

[57] ABSTRACT

Eye and head movements produce large voltages which obscure the electrical activity of the brain, interfering with diagnostic procedures. In the system and method of the present invention electrical response to such movement artifact is detected by a set of electrodes and transmitted to amplifiers, analog-to-digital converters and an on-line to a digital computer. The computer monitors each of the 19 channels corresponding to the 19 electrodes on the subject's head and a pair of electrodes located diagonally above and below one eye (trans-orbital) to detect artifacts associated with eye movement. Each channel of brain waves and artifact signals, converted into digital information, are compared with a threshold selected digital value set by the operator either by using standard values, by empirically eliciting sample artifacts, or by a standard deviation determination. The computer, after determining that there exists a movement artifact, i.e., an artifact in excess of the digital threshold value, either blanks out the brain wave data for that period or magnetically "marks" the appropriate channel(s) of the multi-channel recording at the time corresponding to the artifact distortion, which may be in all or only some channels.

5 Claims, 6 Drawing Figures

PREVENTION OF DISTORTION OF BRAINWAVE DATA DUE TO EYE MOVEMENT OR OTHER ARTIFACTS

The Government has rights in this invention pursuant to Grant Number ERP 03494 awarded by the National Science Foundation.

BACKGROUND OF THE INVENTION

The present invention relates to electroencephalography and more particularly to the suppression of the confounding effects of artifacts resulting from eye and head movements (class 1282.1 B).

At the present time it is known that it is possible to observe and record a subject's brain waves by attaching a number of removable electrodes to the subject's scalp. The subject's brain waves, at the present time, are generally recorded on a paper strip chart in analog form and analyzed by being viewed by a trained clinical neurologist.

It has also been suggested that subjects' brain waves may be analyzed by various analog type computers and by utilization of digital computers using special algorithms.

If the subject under tests moves or blinks, or even if his eyes move, the electrodes connected to his scalp may detect a large electrical response which may be confused as being a brain wave signal. A movement artifact may be distinguished from a brain wave by one or another of the following characteristics: (i) it is a large signal beyond normal excursion limits, (ii) it is unusually widespread and rapid event, as shown by its first derivative, or (iii) it has a power spectrum with most of the energy between 0.5 and 1.1 Hz.

In some systems of testing it is desirable to obtain the subject's "evoked response," the subject's brain waves, in response to a known and selectively timed stimulus such as a light flash or an auditory click. It may happen, however, that the stimulation which gives rise to the brain wave response also also provokes a movement artifact, that is, the subject may blink, move his eyes or his head, creating an electrical signal which may be mistaken as a brain wave. Such artifacts usually appear at the same time across multiple recording electrodes.

The literature discloses that artifact compensation in EEG (electroencephalography) has been accomplished through a number of methods. In 1975 Huang and Flynn suggested placing the detection electrode a distance of 3–4 mm from the signal source to achieve pronounced muscle artifact attenuation, see *Electroencephalography and Clinical Neurophysiology*, "Recording of Single Unit Activity During Electrical Stimulation and Microintophoresis, 1977." Rex Y. Wang and George K. Aghajahian suggest use of a differential amplifier in combination with a recording and an indifferent electrode so that the common signal, noise-artfact, is canceled (Id). They also suggest placing two detection electrodes in close opposition to the signal source to achieve the ideal differential recording in which the stimulus artifacts will match and cancel (Id). Artifact distortion may be reduced by signal averaging or common mode identification methods, but it has been suggested that neither is adequate where the signal is continuous. *Journal of Electrophysiological Technology*, "Computers in Neurophysiology," C. D. Binnie.

In U.S. Pat. No. 3,893,450 entitled "Method and Apparatus for Brain Waveform Examination," there is mentioned, at column 1, lines 36–41, that artifacts that impede the measurement of brain responses to stimulation are one of the four general problems in accurate EEG analysis. In U.S. Pat. No. 3,774,593 entitled "Method of and Apparatus For Sleep Monitoring By Brainwave Electromyographic and Eye Movement Signals" there is disclosed a set of two electrodes for picking up eye movement (EM) secured on the temple portions of the subject. A special electrical cable design to suppress artifact is described in Pryzbylik, "Low Noise Cable and Slip Ring Assembly For Recording of Small-Amplitude Physiological Signals in Chronic Animals," *Medical and Biological Eng.*, Vol. 14, No. 5, pp. 565–569, Sept. 1976. The article Gevins et al, "Automated Analysis of the Electrical Activity Of the Human Brain (EEG): A Progress Report, "*IEEE Proceedings*, Vol. 63, No. 10, Oct. 1975, at page 1392 generally describes a method of artifact rejection in which the intensity of the electrical signal representing the artifact is compared with a threshold value set during initial calibration. The data being collected is discarded until the voltage representing the artifact falls to below the threshold value.

The use of various systems of electrode placement, including the use of an electrode cap as shown in U.S. Pat. No. 3,998,213, has been suggested and the problem of electrode systems for active subjects such as hyperactive children has also been explored, see Hanley et al, "Electrode Systems For Recording The EEG In Active Subjects," *Biomedical Electrotechnology*, Academic Press 1974. However, the use of special electrodes and the placement of the electrodes does not markedly reduce the adverse effects from the subject's movement. In U.S. Pat. No. 3,841,309 an "adjustable threshold device" is used in an EEG system to determine the timing between brain wave detected peaks in an EEG channel.

FEATURES AND OBJECTIVES OF THE INVENTION

It is a feature of the present invention to provide a method in electroencephalography to decrease those adverse effects which arise from muscle artifact of the subject under test during the recording of the subject's brain waves. The method includes a number of steps, including removably attaching a brain wave detection electrode to the scalp of the subject under test. That electrode detects the subject's brain waves and produces an electrical signal corresponding to those brain waves. The next step is to removably attach two muscle artifact electrodes across one of the subject's eyes in a trans-orbital position which detect changes in the dipolar field of the eye and other voltages related to eye movement which produce artifacts, producing electrical signals corresponding to these artifacts. The electrical signals from the brain wave electrode are amplified, put into digital form and transmitted to a digital computer. The movement artifact signals are amplified, placed into digital form and used, if in excess of a threshold value, to modify the record of the amplified brain wave signals. For example, a suitable modification is to record the movement artifact signals on the same recording and in synchronized relationship with the recording of the simultaneous brain wave signals. A threshold value is set by an operator who regards the brain wave and movement artifact signals with the subject at rest and pushes a button to enter the rest conditions as normal. A digital computer automatically computes a standard deviation from the normal amplitude range, for example, of eight, which is then defined as the threshold value. Another method is to set thresholds by successive computer instructions until artifacts produced by deliberately produced movements are detected. Another method is to use a set of preset threshold values ascertained by experience.

It is a further feature of the present invention to provide an electroencephalographic system to decrease adverse effects from movement artifact of the subject under test during the recording of the subject's brain waves. The system includes a removably attachable brain wave detection electrode adapted to be attached to the scalp of the subject to detect the subject's brain waves and produce an electrical signal corresponding to the brain waves, and an amplifier connected to the brain wave electrode to amplify its electrical signals. The system also includes two removably attachable movement artifact electrodes which are attached across one of the subject's eyes in a transorbital position to detect muscle artifact and produce electrical signals corresponding to eye or eyelid movements and an amplifier connected to the artifact electrodes to amplify their signals. A first analog-to-digital converter converts the brain wave signals into digital form and a second analog-to-digital converter converts the artifact signals into digital form. The system further includes means to select a minimum standard, i.e., a threshold value, in digital form for the artifact signals based upon an automatically computed standard deviation and means to modify the amplified brain wave signals based upon said amplified artifact signals in excess of said minimum standard. Such modification may consist of rejection of brain wave data recorded during periods when movements of head or eyes generated voltages which could contaminate the recorded brain signals, or to magnetically mark those portions of a sample of brain waves recorded from one or many electrode derivations where such contamination is suspected.

It is an objective of the present invention to provide a system for the recording and analysis of brain waves which will be relatively less subject to eye movement and muscle artifacts associated with the eye region.

It is a further objective of the present invention to provide such a system which may be applied to the subject under test painlessly and without undue discomfort and may be applied in a relatively simple and convenient manner.

It is a further objective of the present invention to provide such a system in which the recording of the brain wave will automatically take account of movement artifacts.

BRIEF DESCRIPTION OF THE DRAWINGS

Other objectives and features of the present invention will be apparent from the following detailed description of the inventor's best present mode of practicing the invention, which description should be taken in conjunction with the accompanying drawings.

In the drawings.

DETAILED DESCRIPTION OF THE INVENTION

Figure 1:
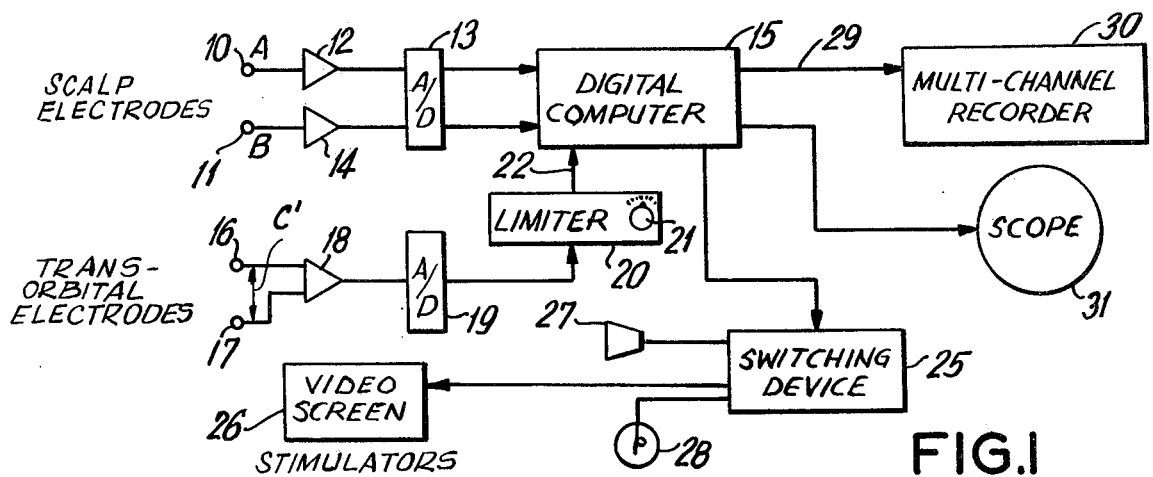
FIG. 1 is a block diagram of a system according to the present invention.
Figure 2:
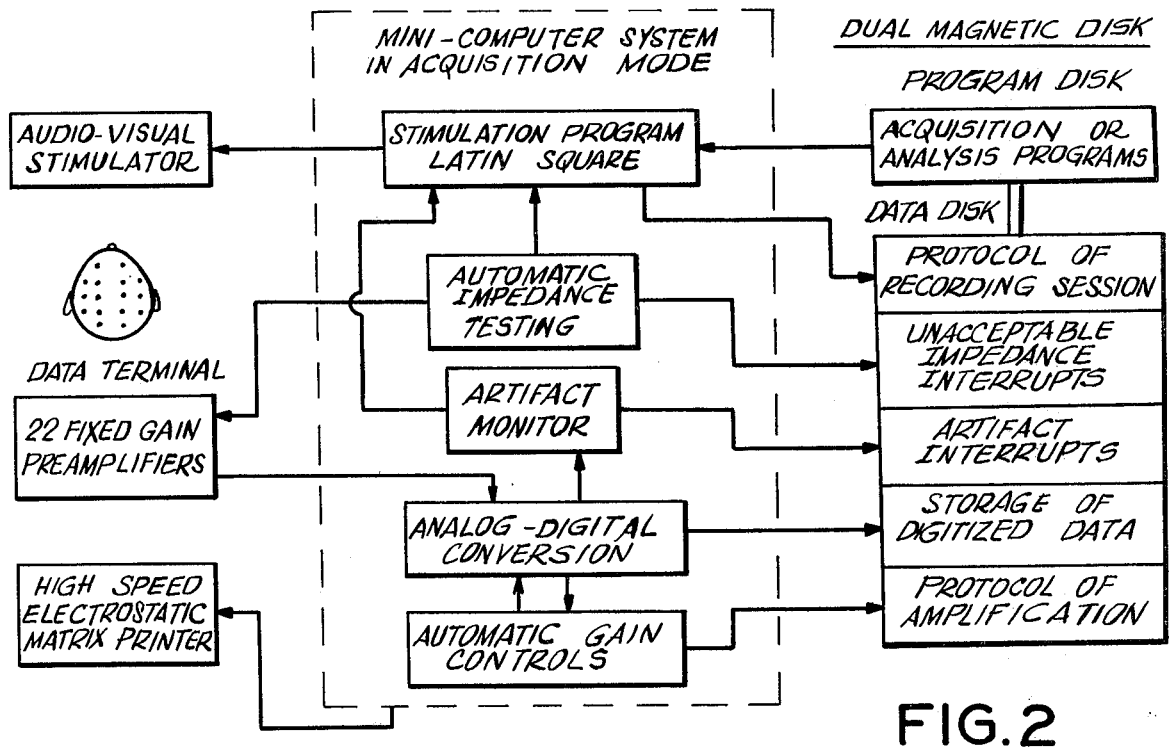
FIG. 2 is a block circuit diagram showing other features of the present invention.

A block circuit diagram of one system utilizing the present invention is illustrated in FIG. 1. In that figure a pair of electrodes 10 and 11, labeled respectively electrodes A and B, are connected to the scalp of the subject under test. Although only two electrodes are shown in practice, generally more electrodes will be used; for example, 19 such electrodes would be connected in fixed positions to the scalp. Such electrodes and their methods of connection to the scalp are well-known in the EEG (electroencephalography) field. The electrode 10 is connected through amplifier 12 to the analog-to-digital converter 13. Similarly, the electrode 11 is connected through the amplifier 14 to the analog-to-digital converter 13.

The analog-to-digital converter 13 converts each of the channels of information from the respective electrodes 10 and 11 from the amplified analog form as received from the respective amplifiers 12 and 14 to digital form. The analog-to-digital converter 13 is connected to a digital computer 15 which is connected to a multi-channel recorder 30, preferably a magnetic disk recorder, although other types, such as magnetic tape recorders, may alternatively be utilized.

In addition to the plurality of scalp electrodes 11, there is also provided a pair of trans-orbital electrodes 16 and 17. These electrodes are positioned opposite each other across one of the eyes of the subject under test. For example, the electrode 16 may be positioned above the right eye and electrode 17 may be positioned below the right eye. The electrodes are removably connected using conductive paste.

It has been found that an electrical signal is produced upon eye movement or by other muscle artifact which is associated with the region of the eye, such as blinking or squinting.

It is theorized that the electrical signal may be due to the change in impedance between the electrodes and may also be partially due to an electrical signal produced by changes in the eye region, such as rotation of the electrical dipole of the eye. The impedance change may arise because eye movement changes the shape of the eyeball, thus lessening the capacitance between the two electrodes. The dipole effect is probably due to voltages across the retina. The electrical signal between the two electrodes is labeled C'. That electrical signal is amplified through difference amplifier 18 and the amplified difference signal is transmitted to analog-to-digital converter 19. The analog-to-digital converter changes the analog difference signal into a digital number which is transmitted to the limiter 20. The limiter 20, which may be a portion or function of the digital computer 15, may be set by the technician utilizing an input teletype connected to digital computer 15 or the dial 21 on the limiter 20 or may be preset by the computer program at usual values. The limiter 20 transmits a warning signal on line 22 to the computer 15 when the number received from the analog-to-digital converter 19 exceeds a certain number selected by the limiter, i.e., a digital threshold value. Upon such a signal the digital computer 15 sends a marking signal on line 29 to the multi-channel recorder 30 or the recording will be interrupted. The threshold value determines whether and how the EEG signals will be stored in the recorder 30; that is, only data occurring during periods without artifact or with artifact below the threshold, the selected number determined by the limiter, will be accepted for storage. All other data will be rejected or marked as suspect.

A program of the computer 15 sets up the various program routines or challenges to the subject under test. It controls the switching device 25 and the stimulators which may include video screen 26 and loudspeaker 27 and light device 28. The computer 15 is also connected by line 29 to the multi-channel recorder 30 so that the recorder 30 makes a record of the challenge being presented simultaneously with the record of the response to that challenge as recorded from the scalp electrodes 10 and 11. The multi-channel recorder 30 is connected for playback purposes to an average response computer and to a computer for comparison with norms. The recorder 30 may produce a magnetic disk or other recording which may be physically taken to a remote data processing facility for analysis. The present invention is not concerned with the methods of analysis of the digital recording of the subject's brain waves either by the average response computer or the comparison with norms computation. However, an extensive discussion of suitable computation methods will be found in the present inventor's book entitled, *Neurometrics: Clinical Applications of Quantitative Electrophysiology*, published 1977 by Erlbaum Associates, and particularly its chapters 5, 6, 7 and 8.

Figure 3:
FIG. 3 is an idealized wave form diagram showing the brain wave recorded from one electrode and the effect due to a simultaneous response and the effect due to movement artifact simultaneously with such response.

An idealized wave form showing the effect of a stimulus on a brain wave is shown in FIG. 3. As shown in that figure, at the left side there is a brain wave response which may be detected in response to a stimulus such as a click or a light flash. The shape, duration and amplitude of a movement artifact may vary in a random manner. However, as shown on the right side of FIG. 3, it often occurs that the effect of movement artifact causes similar electrical events as a brain wave, at an electrode which is connected to the scalp. In other words, the scalp electrode and its associated amplifiers alone offer no way to distinguish a brain wave which is the response to a stimulus from the electrical activity caused by a movement artifact. The same holds true for the spontaneous EEG. In other words, this distinction requires some sort of analytic procedure or circuitry.

Figure 4:
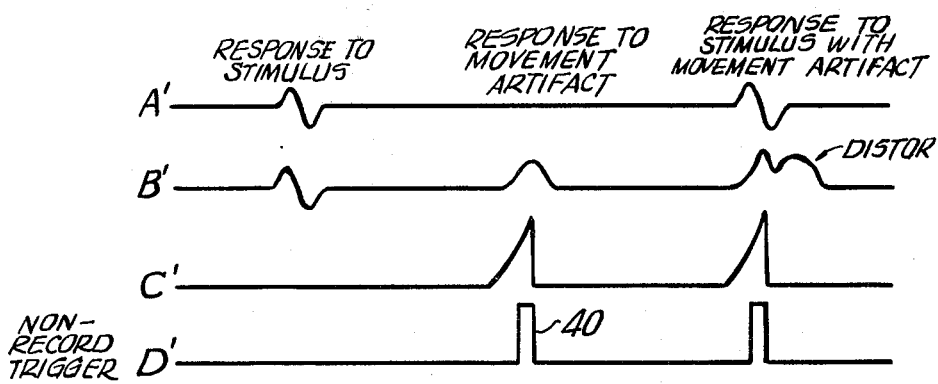
FIG. 4 shows an idealized illustration of recordings in four channels of brain waves and movement artifact.

FIG. 4 shows three analog recording channels under idealized conditions, showing at the left the response to a stimulus, in the center to movement artifact, and at the right to a stimulus accompanied by movement. These channels are shown in analog form only for purposes of illustration, but in practice would preferably be recorded in digital form. In other words, although FIG. 4 illustrates the point with an analog response of the type which would be drawn on paper by a conventional EEG machine, it must be understood that in the system of FIG. 1 the recording is of the corresponding digital representation. By the word "stimulus" is meant in this context an external event such as an auditory click or a light flash. As shown, the brain wave response evoked by this stimulus is detected by electrodes 10,11 and the corresponding channels A', B' amplify and record the brain wave under that condition, i.e., the channels A' and B' record the amplified response from electrodes 10 and 11. Channel C' corresponds to the artifact electrical signal from the trans-orbital electrodes 16, 17 under conditions of eye movement. Again, for purpose of illustration only, the movement artifact effect is shown as an analog signal consisting of spikes of relatively large amplitude and short duration. In response to those spikes the limiter 20, which would include a trigger switch at its output, produces a signal 40 which is recorded on the channel D' of the multi-channel recorder 30.

Figure 6:
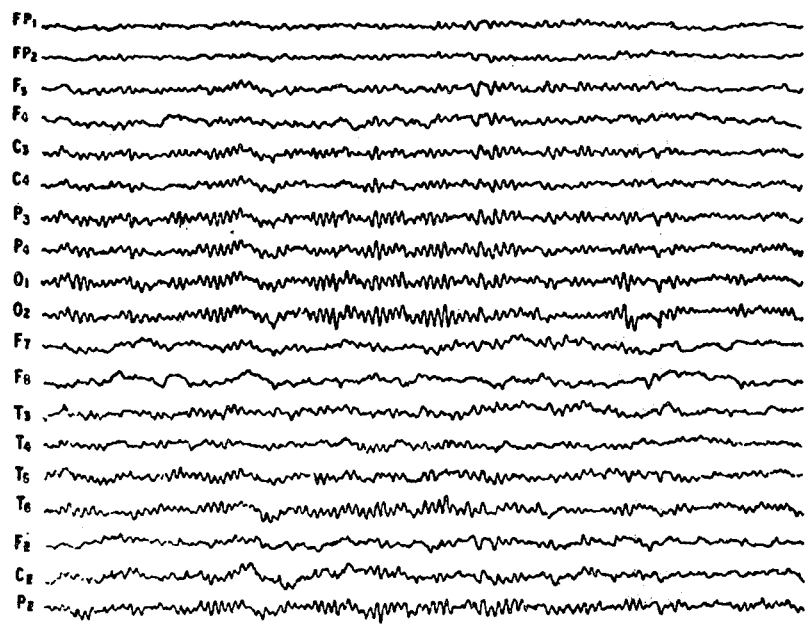
FIG. 6 is an actual illustration of computer generated EEG with the artifact suppressed.

In one embodiment, producing records as illustrated in FIG. 6, the recording is blanked out for a certain time period if movement artifact above the threshold occurs, the period preferably being the duration of movement artifact and one second after.

In operation, the technician connects the electrodes 10, 11, 16, 17 to the subject and then monitors the oscilloscope 31. The oscilloscope traces are monitored when the subject is at rest and also when he moves his eyes, his head, etc. Each brain wave electrode and the EM artifact electrodes 16,17 may be shown independently or compared simultaneously on the oscilloscope 31. When the traces on the oscilloscope 31, which are digital displays from computer 15, show the subject is at rest, i.e., without artifact, the technician, in effect, pushes a button to establish such data as the base line. Usually the artifact EM channel (electrodes 16,17) is compared to the major focus of interest in the brain wave activity, which is often the region primarily responsive to a stimulus of a particular sense modality. The input device to the computer 15 may be a teletype, in which case the base line may be established by entry of an appropriate key. That base line, in digital value form, is automatically used to compute the standard deviation of the brain activity in the absence of artifact. The means amplitude of the baseline plus or minus a voltage equal to a criterion multiple of standard deviations then defines the threshold value. A common multiple is 4–5 standard deviations.

Figure 5:
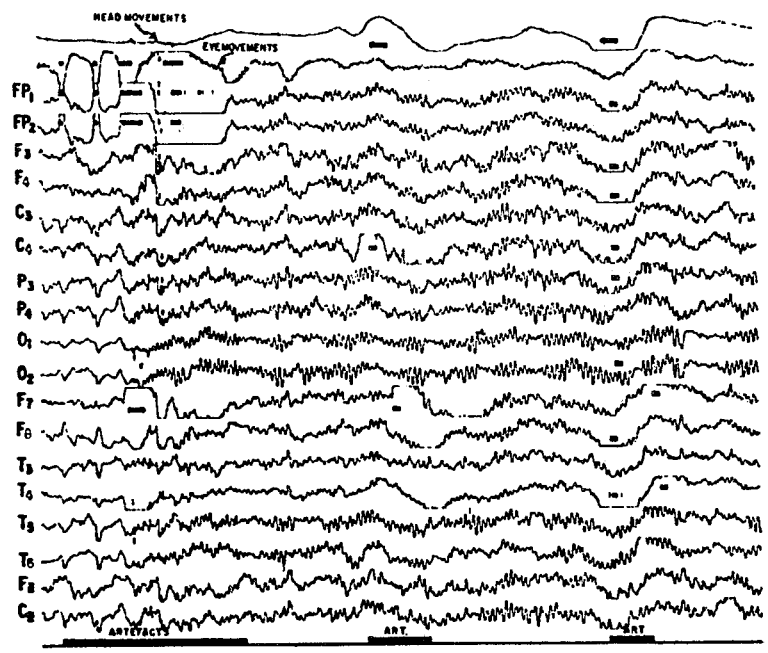
FIG. 5 is an actual illustration of computer generated EEG with the presence of artifact.

If the EM electrodes 16,17, or any of the other electrodes, produce a transient large event, i.e., a digital value in excess of the digital threshold value (defined by the selected standard deviation) the brain wave record is modified. For example, in the embodiment shown in FIG. 6 the brain waves are not recorded during the period while the movement artifact is above the threshold value and for one second afterwards, to allow time for the amplifiers to return to normal range. In another embodiment, shown in FIG. 5, the brain waves are recorded together with a marker indicating the time and electrode recording channel positions showing movement artifact.

What is claimed is:

1. A method in electroencephalography to decrease misleading effects from movement artifacts arising from the subject under test during the recording of the subject's brain waves, including the steps of:
    removably attaching a brain wave detection electrode to the scalp of the subject under test to detect the subject's brain waves and produce an electrical signal corresponding to said brain waves;
    removably attaching two muscle artifact electrodes across one of the subject's eyes in a trans-orbital position to detect movement artifact and produce electrical signals corresponding to said detected movement artifact;

amplifying the said electrical signals from the brain wave electrode and converting the amplified brain wave signals into digital form;

amplifying the said movement artifact signals and converting the amplified signals into digital form;

establishing a threshold value in digital form of artifact activity by establishing a set of rest values for artifact and brain wave activity and automatically obtaining or arbitrarily defining a predetermined deviation therefrom;

modifying the amplified brain wave signals when said amplified movement artifact signals exceed said established threshold value; and recording said modified brain wave signals.

2. The method of claim 1, wherein said modification is the use of those movement artifact signals in excess of the threshold to blank out the recording of the simultaneously occurring brain waves.

3. A method in electroencephalography to decrease misleading effects from movement artifacts arising from the subject under test during the recording of the subject's brain waves, including the steps of:

removably attaching a brain wave detection electrode to the scalp of the subject under test to detect the subject's brain waves and produce an electrical signal corresponding to said brain waves;

removably attaching two muscle artifact electrodes across one of the subject's eyes in a trans-orbital position to detect movement artifact and produce electrical signals corresponding to said detected movement artifact;

amplifying the said electrical signals from the brain wave electrode and converting the amplified brain wave signals into digital form;

amplifying the said movement artifact signals and converting the amplified signals into digital form;

establishing a threshold value in digital form of artifact activity by establishing a set of rest values for artifact and brain wave activity and automatically obtaining or arbitrarily defining a predetermined deviation therefrom;

marking the amplified brain wave signals when said amplified movement artifact signals exceed said established threshold value; and recording said marked brain wave signals.

4. An electroencephalographic system to decrease misleading effects from movement artifact of the subject under test during the recording of the subject's brain waves, including:

a removably attachable brain wave detection electrode adapted to be attached to the scalp of the subject under test to detect the subject's brain waves and produce an electrical signal corresponding to said brain waves;

two removably attachable movement artifact electrodes which are attached across one of the subject's eyes in a transorbital position to detect movement and produce electrical signals corresponding to said movement;

an amplifier connected to said brain wave electrode to amplify the said electrical signals from the brain wave electrode;

a first analog-to-digital converter to convert said brain wave signals into digital form;

an amplifier connected to said movement artifact electrodes to amplify the said movement artifact signals;

a second analog-to-digital converter to convert said movement artifact signals into digital form;

means to determine base line values for said movement artifact and brain wave signals based upon the subjects at rest;

means to automatically fix a minimum threshold in digital form for said movement artifact signals based upon a selected statistical standard and said base line values;

means to modify the amplified brain wave signals based upon said amplified movement artifact signals in excess of said threshold; and means to record said modified brain wave signals.

5. A system as in claim 4 and further including a digital computer connected to said analog-to-digital converters and a multi-channel recorder connected to said digital computer to record the same amplified brain wave and movement artifact signals in parallel tracks on the same record.

* * * * *